1## United States Patent

Bunner et al.

(10) Patent No.: US 9,304,115 B2
(45) Date of Patent: Apr. 5, 2016

(54) PRESSURE SENSING AND FLOW CONTROL IN DIFFUSION-BONDED PLANAR DEVICES FOR FLUID CHROMATOGRAPHY

(75) Inventors: Bernard Bunner, Cambridge, MA (US); Geoff C. Gerhardt, Millbury, MA (US); Theodore A. Dourdeville, Marion, MA (US)

(73) Assignee: Waters Technologies Corporation, Milford, MA (US)

( * ) Notice: Subject to any disclaimer, the term of this patent is extended or adjusted under 35 U.S.C. 154(b) by 573 days.

(21) Appl. No.: 13/696,965

(22) PCT Filed: May 10, 2011

(86) PCT No.: PCT/US2011/035988
§ 371 (c)(1),
(2), (4) Date: Feb. 14, 2013

(87) PCT Pub. No.: WO2011/143268
PCT Pub. Date: Nov. 17, 2011

(65) Prior Publication Data
US 2013/0133760 A1 May 30, 2013

Related U.S. Application Data

(60) Provisional application No. 61/332,842, filed on May 10, 2010.

(51) Int. Cl.
| G01N 30/00 | (2006.01) |
| G01N 30/32 | (2006.01) |
| G01N 30/34 | (2006.01) |
| G01L 15/00 | (2006.01) |
| G01L 19/00 | (2006.01) |

(Continued)

(52) U.S. Cl.
CPC ............. *G01N 30/00* (2013.01); *G01L 9/0026* (2013.01); *G01L 9/0042* (2013.01); *G01L 15/00* (2013.01); *G01L 19/0023* (2013.01); *G01N 30/32* (2013.01); *G01N 30/34* (2013.01);
(Continued)

(58) Field of Classification Search
None
See application file for complete search history.

(56) References Cited

U.S. PATENT DOCUMENTS

| 5,412,994 A | 5/1995 | Cook et al. |
| 5,537,860 A | 7/1996 | Haertl |

(Continued)

FOREIGN PATENT DOCUMENTS

| JP | 08313505 A | 11/1996 |
| WO | WO2008/106613 A2 | 9/2008 |
| WO | WO2009/053915 A1 | 4/2009 |

OTHER PUBLICATIONS

International Search Report and Written Opinion from PCT/US2011/035988 mailed Aug. 9, 2011.

*Primary Examiner* — Andre Allen
(74) *Attorney, Agent, or Firm* — McCarter & English, LLP; Deborah M. Vernon

(57) ABSTRACT

Flow through pressure sensors for use in fluid chromatography systems include a planar device formed from diffusion bonding of a plurality of metallic sheets and at least one sensing element. The planar device has a top surface, a bottom surface and a flow through channel. A diaphragm formed from a portion of one of the top or bottom surfaces is located adjacent to a sensing region of the flow through channel and is attached to the sensing element. The diaphragm is sized to deflect a distance in response to fluid pressure in the sensing region, which has an internal volume of less than about 25 microliters. The diaphragm and attached sensing element form a pressure sensor that measures strain or deflection of the diaphragm to calculate a pressure within the sensing region.

24 Claims, 12 Drawing Sheets

(51) Int. Cl.
*G05D 7/06* (2006.01)
*G01L 9/00* (2006.01)
*B01D 15/16* (2006.01)
*B01L 3/00* (2006.01)

(52) U.S. Cl.
CPC ........... *G05D 7/0676* (2013.01); *B01D 15/163* (2013.01); *B01L 3/502746* (2013.01); *B01L 2200/146* (2013.01); *B01L 2300/0663* (2013.01); *B01L 2300/0867* (2013.01); *B01L 2300/0883* (2013.01); *B01L 2400/0487* (2013.01); *B01L 2400/086* (2013.01); *G01L 9/0055* (2013.01); *Y10T 137/7762* (2015.04)

(56) References Cited

U.S. PATENT DOCUMENTS

| | | | |
|---|---|---|---|
| 5,767,387 A * | 6/1998 | Wang | 73/23.42 |
| 6,467,354 B1 | 10/2002 | Allen | |
| 6,945,116 B2 | 9/2005 | Xie et al. | |
| 7,674,375 B2 | 3/2010 | Gerhardt et al. | |
| 8,020,750 B2 * | 9/2011 | Crockett et al. | 228/193 |
| 2005/0223783 A1 | 10/2005 | Spivak | |
| 2006/0260408 A1 | 11/2006 | Villa et al. | |
| 2008/0296351 A1 * | 12/2008 | Crockett et al. | 228/164 |
| 2009/0064790 A1 | 3/2009 | Davidovits et al. | |

* cited by examiner

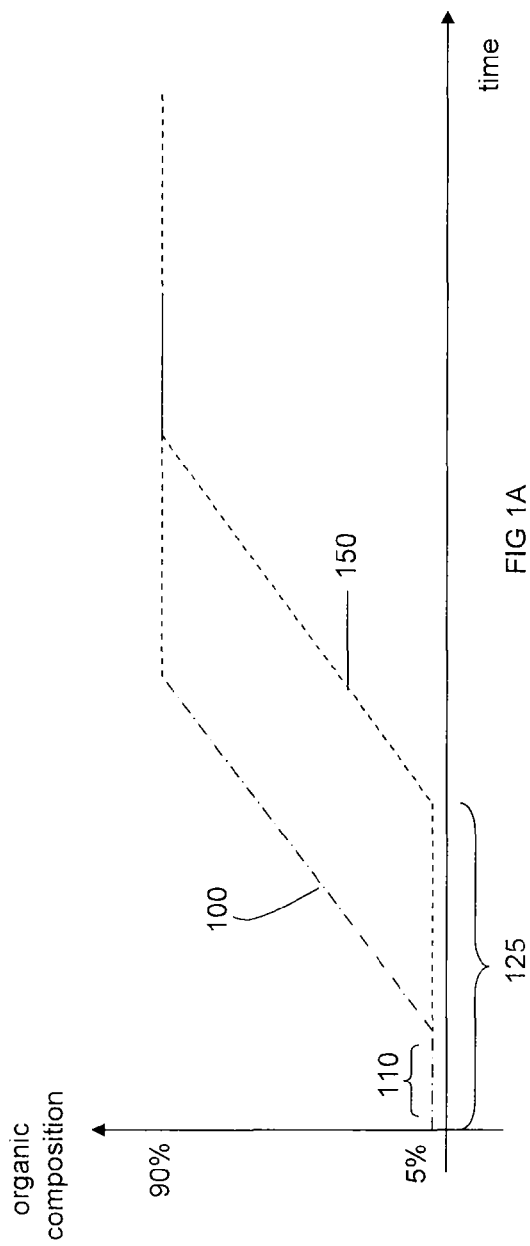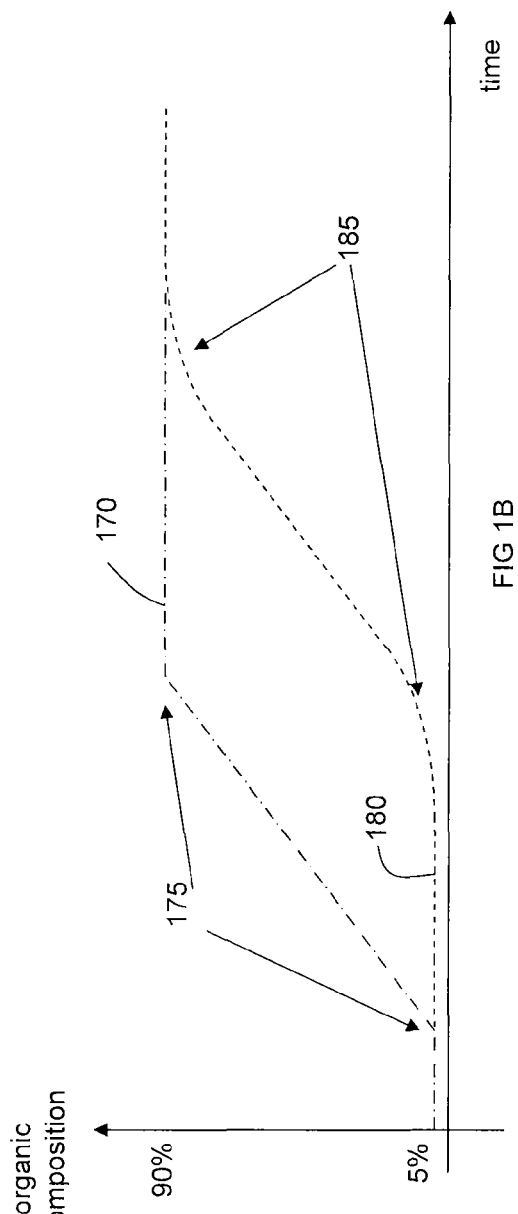

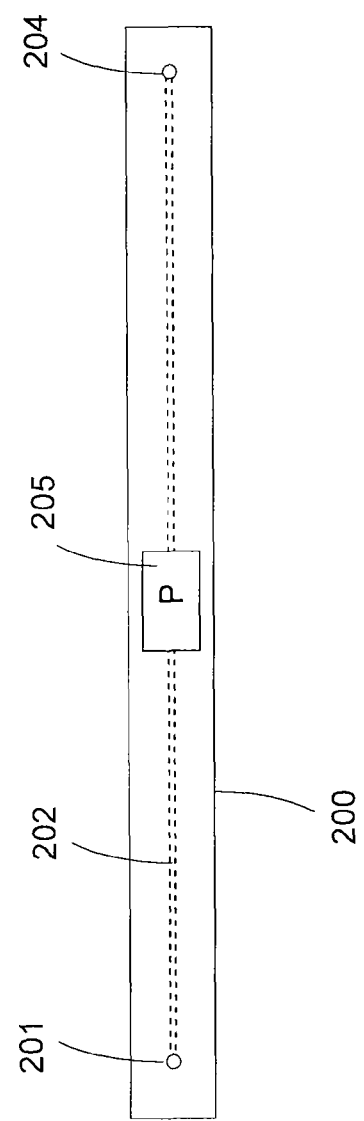

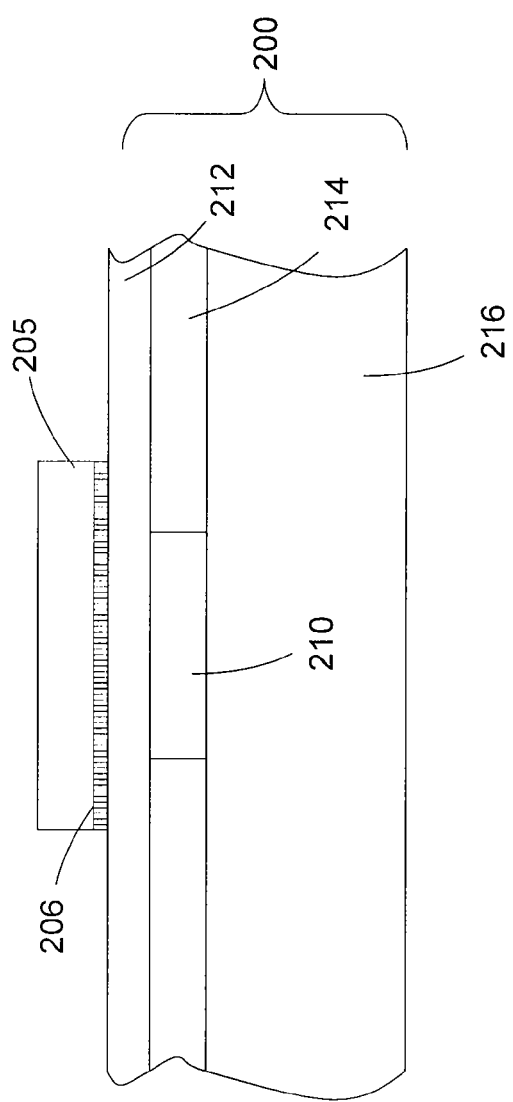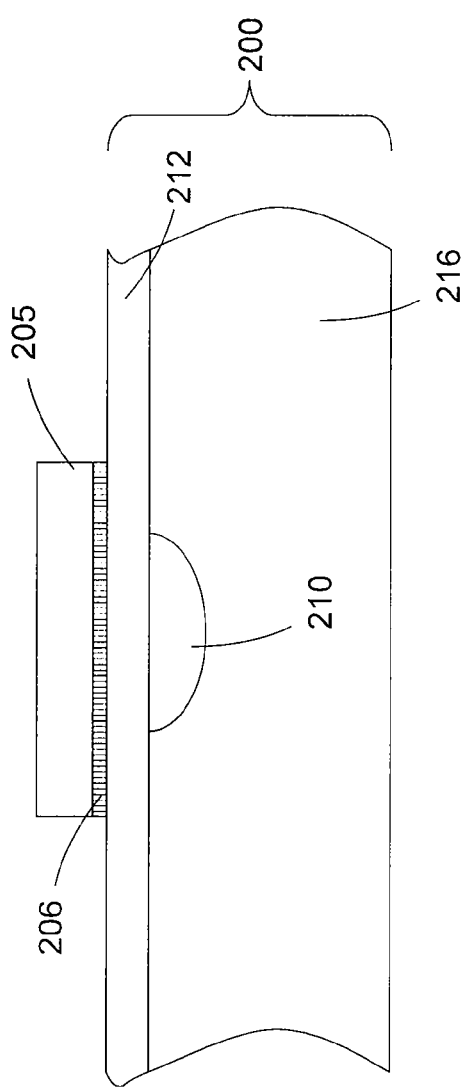

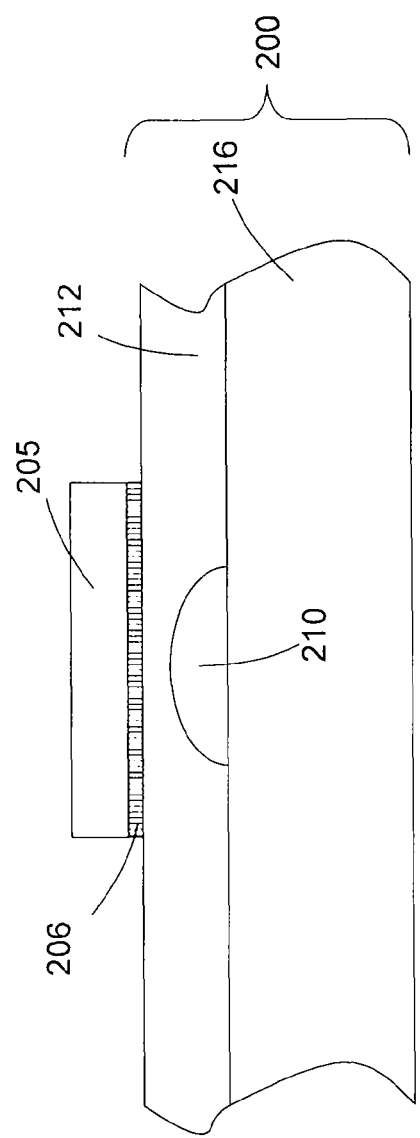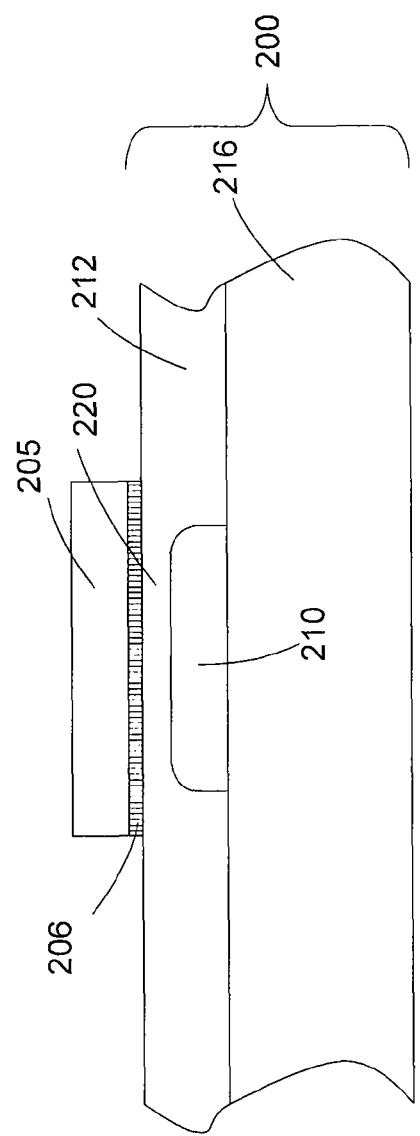

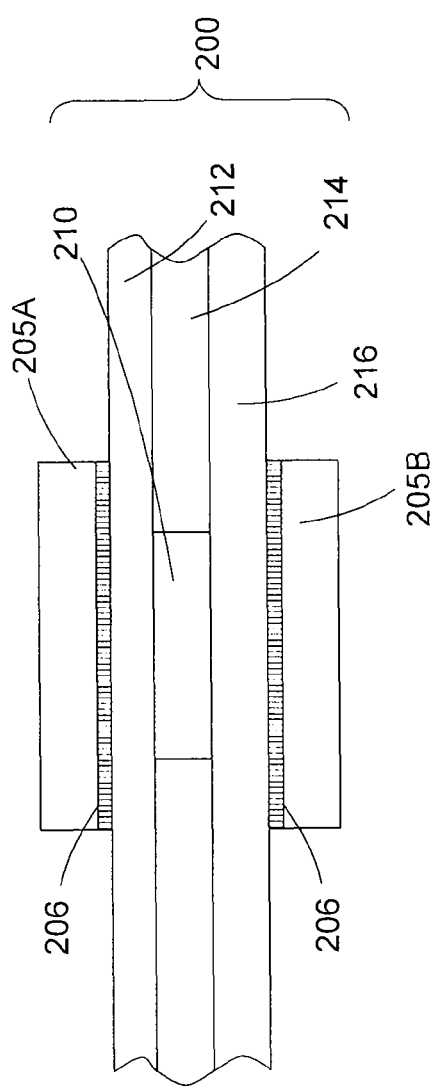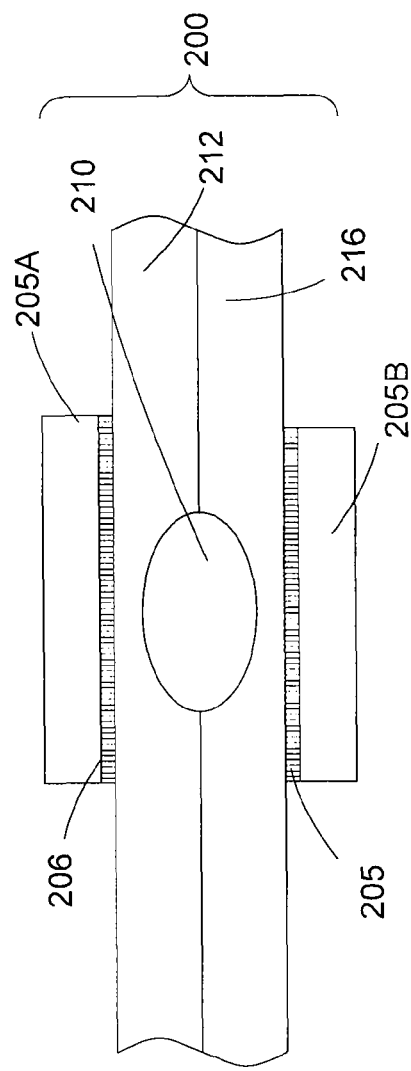

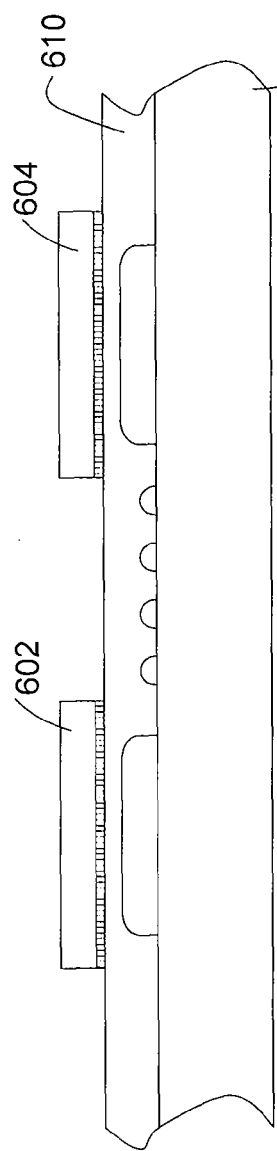
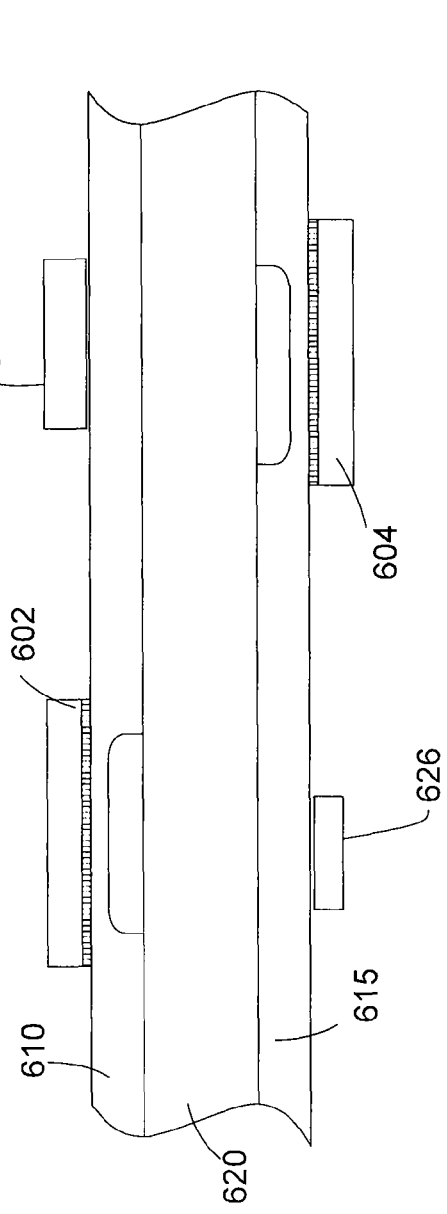

PRESSURE SENSING AND FLOW CONTROL IN DIFFUSION-BONDED PLANAR DEVICES FOR FLUID CHROMATOGRAPHY

RELATED APPLICATIONS

This application is a National Stage Application of International Application Number PCT/US2011/035988, filed on May 10, 2011, which claims the benefit of and priority to U.S. Provisional Application No. 61/332,842, filed May 10, 2010, both of which are owned by the assignee of the instant application and the disclosures of which are hereby incorporated by reference in their entirety.

TECHNICAL FIELD

The technology generally relates to devices used in fluid chromatography systems, and, in particular, to high-pressure fluid chromatography instruments with low flow rates.

BACKGROUND INFORMATION

It is advantageous to control flow rate in chromatography instruments (e.g., high-performance liquid chromatography instrument or HPLC, ultra-performance liquid chromatography instrument or UPLC™, or supercritical fluid chromatography instrument or SFC) such that a loss of resolution or information is substantially minimized or avoided. For example, upstream of the point of analyte introduction or "sample injection", in a "gradient mode" of liquid chromatography, solvent composition profiles are generated by pumps and corresponding controllers, where those composition profiles have a time-course and a corresponding volume-course. As the volume scale of chromatography decreases, the volume scale of the gradient profile likewise decreases. Thus in nanoscale chromatography, an entire solvent gradient profile may encompass only a few microliters of liquid volume. Within that few microliters is expected to reside at least a defined linear ramp of solvent composition, or perhaps a staircase of solvent composition steps. Assertion of that solvent composition profile, with good fidelity, onto the chromatography column, requires that the internal volumes of the intervening fluid paths are small relative to the volume of the gradient profile features, and extremely cleanly-swept. In order to improve results it is advantageous to avoid the presence of poorly-swept or "dead" volumes in these liquid systems. Emphasis is placed on the reduction or elimination of dead volumes throughout the chromatography system, to maximize system performance.

To control or monitor the flow through an instrument, it is sometimes desirable to include one or more sensors in communication with the fluid stream(s) used within the instrument. In a large-scale chemical process where one might seek to obtain, for example, a pressure measurement, it is typically straightforward to purchase a commercially-available sensor and to install the sensor into the system using readily available mounting flanges with screw-thread connectors. Many large-scale chemical processes are relatively immune to the introduction of incremental volumes (often milliliters) associated with such a measurement. The cleanliness with which that introduced volume is swept by the process stream may also not be particularly demanding (e.g., in a system where tens or hundreds of liters per minute of process flow exists, a transducer which has a few milliliters of internal volume, which is swept or exchanged once during the passage of a liter or more of the process stream, may be perfectly acceptable.)

One can readily appreciate that in a fluid chromatography instrument where an entire solvent gradient profile may encompass only a few microliters of volume, up to as much as a few milliliters of volume, such a transducer implementation is not acceptable.

Most commercially available pressure sensors capable of measurements up to tens or hundreds of megapascals (e.g., high-pressure systems) contain large internal volumes. For example, the PX01 pressure transducer sold by Omega Engineering, Inc., (Stamford, Conn., USA) which is capable of measurement up to 200 megapascals (MPa), has an internal volume of 0.51 mililiter. HPLC solvent delivery systems, which may include multiple pumps sourcing respective mobile phases, typically generate a mixture of two liquids, such as water and an organic solvent in the case of reversed-phase chromatography. In a gradient mode of chromatography, the two liquids are pumped at flow rates that vary over the course of a separation, with the respective flow rates corresponding to programmed profiles. Assume that a separation is performed at a constant flow rate of 4 microliter/minute and that its duration is 5 minutes, over which time the composition of the mobile phase being delivered to the chromatographic column is supposed to vary linearly from 5% organic solvent to 90% organic solvent. This is illustrated schematically in FIG. 1A, where the percentage of organic solvent, measured slightly ahead of the column, is plotted versus time (dash-dotted line 100). At time t=0, the pump controller receives the command to begin a linear ramp from 5% to 90% organic solvent composition. Because of the internal volume of the pump, there is a lag 110, commonly referred to as delay time, before the actual beginning of the gradient. This lag is sometimes also expressed in terms of delay volume, which is simply the product of the delay time and the flow rate. For reasons of speed and performance, this delay time should ideally be as small as possible. If a sensor with a large internal volume is located between the pump and the column, the delay time can be significantly increased, as shown schematically by a larger delay time 125 in FIG. 1A for dashed line 150. For example, if the internal volume is 400 microliters and the flow rate is 4 microliter/minute, the delay time would be increased by 100 minutes which is unacceptable in almost all situations, but especially in a separation that is supposed to last only 5 minutes. In such a separation, the delay time is ideally less than one minute, implying a delay volume of less than 4 microliters in this example.

Furthermore, the fluid volume inside commercially available sensors is often poorly swept. For example, the PX01 pressure transducer has only one fluid access port. When it is used to measure the pressure of a mixture of liquids flowing along a tube or channel and when the composition of this mixture changes over time, the liquids flowing along the tube or channel will mix slowly with the liquid contained inside the sensor, which will change the composition of the mixture. This is undesirable in gradient chromatography, where fidelity to a given composition is highly desired. Ideally, as is illustrated in FIG. 1B by the dash-dotted line 170, corners 175 of the linear ramp of a gradient of composition are sharp. If a sensor with a large internal volume and poor sweeping of this internal volume is placed between the pump and the column, the profile of the gradient will be more like dashed line 180 with highly rounded corners 185.

SUMMARY

In general, an aspect of the technology involves incorporation of one or more pressure sensors in an apparatus used in a fluid chromatography system without degrading flow through properties, such as, for example, without significantly increasing an internal wetted volume of the device; without incorporating poorly-swept or dead volume; or without incorporating regions of flow stagnation or recirculation.

In the present technology, diffusion bonding is used to form a device in which one or more sensors can be incorporated. Diffusion bonding, due to its ability to create leak tight (hermetic) seals which can withstand high pressures (e.g., 40 MPa or greater) makes it possible to obtain the following advantageous characteristics for use in fluid chromatography, and particularly in HPLC, UPLC™, or SFC: 1) the ability to incorporate pressure sensors that can measure high pressures, up to 100 MPa or 200 MPa, and withstand burst pressures even larger than those, 2) a small internal volume, below 25 microliter and preferably under 5 microliter, 3) a flow-through design ensuring good sweeping of the internal volume, and 4) high chemical inertness and corrosion resistance to be compatible with the many different fluids used as mobile phases.

In one aspect the technology features a flow through apparatus for use in a system for chromatographic separation. The flow through pressure sensor is able to withstand pressures of at least about 40 MPa. The flow through pressure sensor includes a planar device and a sensing element. The planar device is formed from a plurality of metallic parts attached by diffusion bonding. The planar device has a top surface, a bottom surface, and at least one flow through channel disposed between the top and bottom surfaces. The sensing element is located on a diaphragm formed from a portion of at least one of the top surface or bottom surface of the planar device. The diaphragm bounds one face of a first sensing region of the at least one flow through channel and is sized to deflect a distance in response to fluid pressure in the first sensing region. The first sensing region has an internal volume of about 25 microliters or less.

Embodiments of this aspect of the technology include one or more of the following features. The sensing element is adapted to measure mechanical strain or, in some embodiments, deflection, of the diaphragm for use in calculation fluid pressure in the first sensing region of the at least one flow through channel. The internal volume of the first sensing region has a value between 25 microliters and 5 microliters (e.g., 20 microliters, 15 microliters, 10 microliters, 5 microliters). In other embodiments, the internal volume is between about 5 microliters and 0.5 microliters (e.g., 4 microliters, 3, microliters, 2 microliters, 1 microliter, 0.5 microliter).

Some embodiments of this aspect require the diaphragm to be formed from the top surface of the planar device. In addition, some embodiments also include a second sensing element located on a second diaphragm formed from a portion of the bottom surface of the planar device that opposes the diaphragm formed from the top surface.

Some embodiments of this aspect feature a second sensing element located on a second diaphragm formed from a second portion of at least one of the top or bottom surface of the planar device. The second diaphragm bounds one face of a second sensing region of the at least one flow through channel and is sized to deflect a distance in response to fluid pressure in the second sensing region. The second sensing region, like the first sensing region, has an internal volume of less than about 25 microliters. In some embodiments which include the first and second sensing elements located on first and second diaphragms, respectively, the flow through pressure sensor can further include a flow restrictor positioned between the first and second sensing regions of the flow through channel. In some embodiments, the first and second sensing elements are both located on either the top surface or bottom surface (i.e., on the same side of the planar device). The first and second sensing elements can be at substantially the same temperature (i.e., materials of the planar device and location of the sensing elements selected to allow the devices to be at the substantially the same temperature by thermal conduction.)

Some embodiments of this aspect feature the incorporation of a plurality of sensing elements. Each sensing element is located on its own separate diaphragm formed from a separate portion of at least one of the top or bottom surface of the planar device. Each of the separate diaphragms bounds one face of each separate sensing region of the at least one flow through channel. The internal volume of each of the sensing regions is 25 microliters or less and each of the diaphragms is sized to deflect a distance in response to fluid pressure in the corresponding separate sensing regions of the flow through channel. In some embodiments, each sensing element of the plurality of sensing elements is at substantially the same temperature.

Some embodiments of this aspect feature forming the plurality of metallic parts from a material that is compatible with a fluid mobile phase used in the chromatographic separation. In embodiments, individual metallic parts of the plurality are formed from titanium (e.g., commercially pure titanium) or a titanium alloy (e.g., a titanium alloy having approximately 6% aluminum and 4% vanadium, commonly referred to as Ti-6Al-4V). In some embodiments, the plurality of metallic parts are formed from stainless steels which may derive from the AISI 300 series or 400 series compositions.

Some embodiments of this aspect feature a sensing region defined by a substantially arcuate cross-sectional shape. For example, the first sensing region may be partially circular, circular, partially elliptical, or elliptical. In some embodiments, the first sensing region is defined by a cross-sectional shape free of corners that induce regions of stagnation or recirculating flow.

Some embodiments of this aspect further include a filler member disposed in a sensing region (such as, for example, the first sensing region) to reduce the internal volume to less than about 25 microliters. For example, the filler member can reduce the internal volume of the sensing region from 25 microliters to 5 microliters or less (e.g., 1 microliter, 0.5 microliter).

Some embodiments of this aspect include using the pressure sensor in a system including a liquid chromatographic separation. In these embodiments, the flow through pressure sensor is adapted for operation at a flow rate of less than about 50 microliters/minute. Other embodiments of this aspect include using the pressure sensor in a system including a supercritical fluid chromatographic separation. In these embodiments, the flow through pressure sensor is adapted for operation at a flow rate of less than about 400 microliters/minute (e.g., 300 microliters/minute).

Another aspect of the technology features a flow controller. The flow controller includes a planar device, a fluid pathway, a first sensing element, a second sensing element, a third sensing element, and a controller. The planar device is formed from a plurality of metallic parts attached by diffusion bonding. The planar device has a top surface and a bottom surface. The fluid pathway is defined within the planar device and is in fluid communication with a first fluid inlet for a first solve delivered by a first pump, a second fluid inlet for a second solvent delivered by a second pump and an outlet to a fluid processing system (e.g., a chromatographic system). The fluid pathway includes a fluid stream merging portion, a first portion extending from the first inlet to the fluid stream merging portion and a second portion extending from the second inlet to the fluid stream merging portion. The fluid pathway also includes a first flow restrictor located between the first inlet and the fluid stream merging portion and a second flow restrictor located between the second inlet and the fluid stream merging portion. The first sensing element of the flow controller is located adjacent to the fluid pathway between the first inlet and the first restrictor. The first sensing element is disposed on and attached to a first diaphragm formed from a section of either the top or bottom surface of the planar device. The first sensing element and attached first diaphragm form a first pressure sensor for measuring strain or deflection of the first diaphragm to calculate a pressure in the first portion without substantially increasing an internal wetted volume of the first portion. The second sensing element of the flow controller is located adjacent to the fluid pathway between the second inlet and the second restrictor. The second sensing element is disposed on and attached to a second diaphragm formed from a section of either the top or bottom surface of the planar device. The second sensing element and attached second diaphragm form a second pressure sensor for measuring strain or deflection of the second diaphragm to calculate a pressure in the second portion without substantially increasing an internal wetted volume of the second portion. The third sensing element of the flow controller is located adjacent to the fluid pathway within the fluid stream merging portion. The third sensing element is disposed on and attached to a third diaphragm formed from a third section of either the top or bottom surface of the planar device. The third sensing element and attached third diaphragm forming a third pressure sensor for measuring strain or deflection of the third diaphragm to calculate a pressure in the fluid stream merging portion without substantially increasing an internal wetted volume of the fluid stream merging portion. The controller calculates a first pressure difference between pressure in the fluid stream merging portion and the first portion and a second pressure difference between pressure in the fluid stream merging portion and the second portion. The controller also calculates a flow rate of the first solvent from the first pressure difference and a flow rate of the second solvent from the second pressure difference, and uses the first flow rate to control the first pump and the second flow rate to control the second pump.

Embodiments of this aspect of the technology include one or more of the following features. In some embodiments, the first solvent is a liquid and a flow rate of the first solvent is less than about 50 microliters/minute. In addition, a flow rate of the second solvent can also be less than about 50 microliters/minute. In some embodiments, the first solvent is a supercritical fluid and a flow rate of the first solvent is less than about 400 microliters/minute. Further, in some embodiments the internal wetted volume of the first portion is less than about 25 microliters. Further, the internal wetted volume of the second portion is less than about 25 microliters. And still yet further the internal wetted volume of the fluid mixing portion is less than about 25 microliters.

Some embodiments of this aspect further define the deflection capabilities of the diaphragms. For example, the first diaphragm can be designed to deflect up to about 20 microns in response to fluid pressures in the first portion. It is advantageous to maximize the amount of deflection in order to increase the resolution and accuracy of the strain or deflection measurement of an attached sensing element.

Some embodiments of this aspect of the technology feature a fluid pathway or portions thereof (e.g., first portion, second portion, or fluid stream merging portion) having a substantially arcuate cross-sectional shape. In some embodiments, the fluid pathway or portions thereof (e.g., first portion, second portion or fluid stream merging portion) has a cross-sectional shape free of corners that induce regions of stagnation or recirculation.

Another aspect of the technology features a method of producing a pressure sensor. The method includes: diffusion bonding a plurality of metallic parts to form a substantially planar device including a top surface, a bottom surface, and at least one channel disposed between the top surface and the bottom surface; and attaching a sensing element to either the top surface or the bottom surface of the substantially planar device at a position bounding one face of the at least one channel. The top surface or bottom surface is sized at the position of attachment to deflect in response to fluid pressure in the at least one channel.

Some embodiments of this aspect of the technology include one or more of the following features. The method can further include patterning one or more of the plurality of metallic parts prior to diffusion bonding to form the at least one channel. Patterning may include one or more of the following techniques: chemical etching, electrochemical machining, electric-discharge machining (EDM), electron beam cutting, and/or mechanical milling.

In some embodiments, a portion of the at least one channel is sized to have a wetted volume of 25 microliters or less (e.g., 5 microliters, 0.5 microliters). In some embodiments, a filler member is incorporated into a cavity formed in the patterned one or more plurality of metallic parts to achieve the wetted volume of 25 microliters or less (e.g., 15 microliters, 5 microliters, 1 microliter, 0.5 microliters).

Some embodiments of this aspect feature shaping of the at least one channel (or at least a region or portion thereof) to have a substantially arcuate cross-sectional shape. Shaping can occurring during patterning of the one or more metallic parts. In some embodiments wherein one or more of the metallic parts is patterned to form a cavity forming at least a portion of a channel, the cavity is defined by a cross-sectional shape free of corners that induce regions of stagnation or recirculating flow in a fluid stream.

Some embodiments of this aspect of the technology further include attaching a second sensing element to either the top or bottom surface of the planar device at a second position bounding one face of the at least one channel. The top or bottom surface is sized at this second position to deflect in response to fluid pressure in the at least one channel. In some embodiments, both the sensing element and second sensing element are attached to the top surface. In some embodiments, the first sensing element is attached to the top surface at a first location and a second sensing element is attached to the bottom surface at a second location that opposes the first location.

Some embodiments of this aspect of the technology further define the deflection capabilities of the top or bottom surfaces in response to the fluid pressure. For example, a portion of the top surface can be designed to deflect up to about 20 microns in response to fluid pressures. A larger deflection increases the resolution and accuracy of the strain or deflection measurement of an attached sensing element.

There are numerous advantages of the above aspects of the technology including, but not limited to, the ability to economically fabricate devices capable of withstanding high internal pressures associated with modern small-particle chromatographic separations, particularly in UPLC™. Another advantage of one or more aspects of the present technology is the integration of several sensors and possibly other functionalities (such as, for example, solvent mixing, solvent preheating, sample injection, and/or direct interfacing of a column) on a single device and to connect the sensors and/or functionalities with channels having extremely small volumes, much smaller than the internal volume of the individual sensors and/or devices performing the functionality. As a result, tubings and fittings normally used when connecting separate devices to each other are eliminated, thereby avoiding extra volumes associated with those tubings and fittings. Another advantage is the ability to pattern the fluid pathways in such a way that sharp corners are avoided to provide proper sweeping of the internal cavities. A further advantage of one or more aspects of the present technology includes the ability to measure the pressure and flow rate of the fluid with virtually no interference on the fluid flow. Still yet a further advantage is the ability to achieve equal or substantially equal temperature of the two or more sensing elements or pressure sensors either passively through thermal conduction as the sensors can be placed on the same metallic substrate or actively through the use of a heater and temperature sensor.

BRIEF DESCRIPTION OF THE FIGURES

The advantages of the technology described above, together with further advantages may be better understood by referring to the following description taken in conjunction with the accompanying drawings. The drawings are not necessarily to scale; emphasis instead generally being placed upon illustrating the principles of the technology.

FIG. 1A is a schematic of organic composition versus time in a HPLC separation illustrating a concept of a delay period.

FIG. 1B is another schematic of organic composition versus time in a HPLC separation illustrating how an increase in internal wetted volume and sweeping properties impact separation results.

FIG. 2 is a schematic top view of a pressure sensor according to an embodiment of the present technology.

FIG. 4A is an enlarged cross-sectional view of a portion of the pressure sensor of FIG. 3 taken along line A-A.

FIG. 4B is an enlarged cross-sectional view of a portion of another embodiment of a pressure sensor.

FIG. 4C is an enlarged cross-sectional view of a portion of another embodiment of a pressure sensor.

FIG. 4D is an enlarged cross-sectional view of a portion of another embodiment of a pressure sensor.

FIG. 4E is an enlarged cross-sectional view of a portion of another embodiment of a pressure sensor.

FIG. 4F is an enlarged cross-sectional view of a portion of another embodiment of a pressure sensor.

FIG. 7A is a schematic cross-sectional view of the flow rate monitoring device of FIG. 6 taken along line B-B.

FIG. 7B is a schematic cross-sectional view of another embodiment of a flow rate monitoring device.

DESCRIPTION

Figure 3:
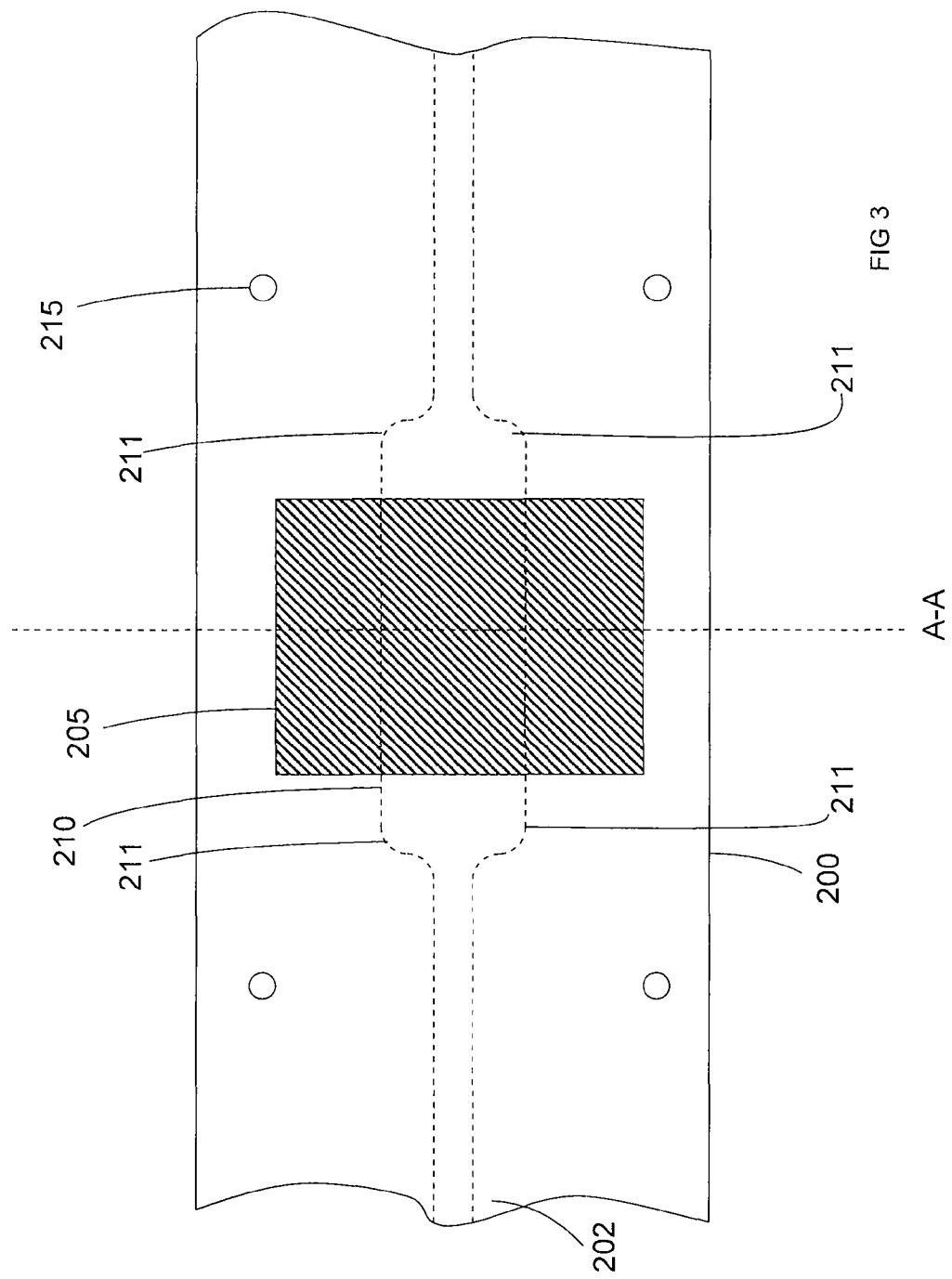
FIG. 3 is an enlarged schematic top view of a portion of the pressure sensor of FIG. 2.

The present technology is directed to integration of one or more pressure sensors in a microfluidic or nanofluidic substrate. In some embodiments, devices with integrated pressure sensors are used in systems including liquid chromatography instruments and are adapted for operation at a flow rate of less than about 50 microliters/minute. In other embodiments, devices with integrated pressure sensors are used in systems including supercritical fluid chromatography instruments and are adapted for operation at a flow rate of less than about 400 microliters/minute. The substrate is a planar device which is diffusion bonded and, in certain embodiments, includes titanium-based and/or iron-based materials. Due to its construction, the substrate with integrated pressure sensor can withstand high pressures (e.g., 40 MPa, 50 MPa, 60 MPa, 70 MPa, 80 MPa, 90 MPa, 100 MPa, or greater), while measuring fluid pressure in small microfluidic/nanofluidic channels. In certain embodiments, the pressure sensors measure fluid pressure in a fluid sensing region having a wetted internal volume of about 25 microliters or less. In certain embodiment the fluid sensing region has a wetted internal volume of about 5 microliters or less. In general, the devices and methods described herein provide for cleanly swept fluid flow properties. In addition, due to the integration of the pressure sensor into the microfluidic/nanofluidic substrate, the devices and methods described herein do not substantially increase the wetted internal volume of the flow through device.

Diffusion bonding entails a combination of vacuum, force, and temperature, to join metallic parts together. The term "diffusion bonding" is sometimes applied to the bonding of dissimilar metals, or even metals with ceramics, where bonding is generally assumed to be due to deformation of surface asperities and the formation of an intimate mechanical contact between the parts. However, in these cases, the strength of the bond can be vastly inferior to that of the constituent metals. The term "diffusion bonding" is sometimes also applied to situations where an intermediate layer, in the form of a thin foil or an electroplated layer, assists in the formation of a bond.

In the present technology, "diffusion bonding" refers to bonding of like metal to like metal, for example pure titanium to pure titanium, or pure titanium to titanium alloy, or stainless steel to stainless steel (e.g., 304 stainless steel to 304 stainless steel or 316 stainless steel to 304 stainless steel).

An appeal of this bonding approach is that the maximum temperature required to achieve a bond is substantially less than the melting temperature of the metals; this can desirably limit the amount of deformation of the parts that are bonded. For example, for titanium, diffusion bonding can be implemented at a temperature of less than 850° C., compared to a melting temperature greater than 1600° C.

Titanium and titanium alloys are uniquely well suited to diffusion bonding because of the high degree of solubility of titanium oxides within bulk titanium, whereas diffusion bonding of other metals, such as stainless steels, is typically more challenging because it is typically more difficult to remove their surface oxide layers.

In addition, Ti-6Al-4V has excellent mechanical properties for making diaphragms or flexures due to its high strength, high elasticity, and strong resistance to fatigue. Those properties allow to design the diaphragm to have both larger deflections and larger number of cycles before failure than if other metals were used.

Titanium, certain titanium alloys, such as, for example, Ti-6Al-4V, and certain 300 series stainless steels, such as, for example, 304 or 316 stainless steels, are also attractive materials because they are to a large extent inert and compatible with the fluid mobile phase(s) used in chromatography. As a result, chemical interactions between the wetted surface of the planar device and the fluid mobile phase are minimized.

Diffusion-bonded microfluidic components are particularly attractive in fluid chromatography applications for several reasons: 1) fluid tight structures capable of withstanding the very high pressures, in excess of 40 MPa or even 100 MPa, desired for some fluid chromatographic instruments, 2) the lack of an intermediate layer, such as a filler material used in brazing, in comparison to some other microfluidic devices, so that the wetted surfaces are chemically uniform, 3) the design freedom to realize complex planar structures, such as folded channels of great length contained in small footprints, or multiple channels connected with extremely small dead volumes, 4) the ability to attach several sensing elements on a single planar substrate, with resulting reduction in number of components and fluidic connections, and hence reduction in potential sources of dead volume and leakage, and 5) the ability to optimize the design of the fluid pathway and mechanical substrate onto which the sensing elements are attached in function of the flow rate or pressure to be measured.

By way of non-limiting examples, a number of embodiments are described below. One of ordinary skill will recognize that these examples are not intended to restrict all embodiments of the technology to any specific set of features or require any specific feature.

EXAMPLE 1

This embodiment includes a planar device allowing fluidic connection and pressure measurement, as illustrated by FIGS. 2, 3, and 4A. Specifically, FIG. 2 is a schematic top view of a pressure sensor in accordance with one embodiment of the present technology. A planar device 200 made by diffusion-bonding contains an internal flow through channel 202 connecting an inlet via 201 and an outlet via 204. The top layer of the planar device, a portion of which is referred to as diaphragm, deflects in response to fluid pressure. The amount of deflection is proportional to the pressure. A sensing element P 205 measures the strain or deflection of the diaphragm and hence provides an estimate of the fluid pressure. The sensing element P 205 can be either a strain gauge, a capacitance sensor, or an optical sensor. A strain gauge sensing element measures the strain in the diaphragm and can be either a glued metal foil strain gauge, such as the one manufactured by Vishay Micro-Measurements, Malvern, Pa., USA, or a glued semiconductor strain gauge, or a thin film strain gauge directly deposited onto the planar device. A capacitance sensor measures the deflection of the diaphragm and can be either a capacitance sensor fabricated by mechanical grinding and machining and glued to the diaphragm, or a thin film capacitive sensor directly deposited on the planar device. An optical sensor measures the deflection of the diaphragm and can be a laser interferometric displacement sensor. Other sensing elements that can measure the mechanical strain or deflection of the diaphragm could be used. Some of the variations are very easily integrated onto planar devices made by diffusion bonding, but are otherwise much more difficult to integrate onto different architectures. For example, while a metal foil strain gauge can be glued to a diaphragm formed in a portion of a surface of the planar device, to incorporate the same metal foil strain gauge in a non-planar device may require the introduction of excess tubing or connection fittings in which the fluid would be diverted. This excess tubing or connection fittings increases the wetted internal volume and as a result, degrades chromatographic separation results as illustrated in FIG. 1B.

FIG. 3 is a top view of a portion of the pressure sensor shown in FIG. 2 in a region around sensing element 205. The width of the flow through channel 202 increases in a small area 210 under the sensing element (e.g., strain gauge) 205. The small area 210 defines a cavity or chamber under the diaphragm where deflection is measured by the sensing element 205 when a pressure is applied in the cavity or chamber. It is understood that the cavity 210 can have an approximately rectangular shape, as shown in FIG. 3, but that its shape can also be circular, partially circular, elliptical, or partially elliptical. The cavity 210 is preferably designed so as to avoid sharp corners that would induce regions of stagnation or recirculating flow. For example, rounded corners 211 result in smooth flow through cavity 210 and proper sweeping of the cavity 210. Registration features, such as holes 215, are possibly used to align the sensing element 205 and the cavity 210 during assembly.

FIG. 4A is a view of an embodiment of a device in accordance with the present technology taken in cross-section along the line A-A shown in FIG. 3. In addition, five further possible embodiments are shown in FIGS. 4B-4F.

Referring to FIG. 4A, planar device is 200 made of three layers 212 (a top surface), 214, and 316 (a bottom surface). Flow through channel 210 has a rectangular or near rectangular cross-section in layer 214 sandwiched between layers 212 and 216, fabricated for instance electric-discharge machining (EDM) or double-sided chemical etching. Pressure in the channel 210 results in upward deflection of a portion of layer 212, also referred to as diaphragm, in the area under sensing element 205. The diaphragm bounds one face of a sensing region of the flow through channel 210. In this example, the sensing element is a strain gauge attached to the diaphragm (i.e., portion of the top layer 212) using a bonding layer or adhesive 206. The width of the channel 210, the thickness of the diaphragm and the material properties of the diaphragm determine the amount of this deflection, given a particular fluid pressure. The first two parameters are design parameters tailored to achieve the maximum amount of deflection or strain that is compatible with the strain gauge, while at the same time preventing mechanical yielding or fatigue failure of the top layer 212. Preferably the bottom layer 216 is thicker than a portion of the top layer 212 (i.e., the diaphragm) so that its deformation is much smaller than that of the top layer. It is understood that the layers 212, 214, and 216 can each consist of one or more physical metallic foils or sheets.

Referring to FIG. 4B, the planar device 200 is made of two layers: top layer 212 and bottom layer 216. A portion of top layer 212 like the embodiment shown in FIG. 4A determines the amount of strain measured by sensing element 205. Flow through channel 210 is created by patterning bottom layer 216. For example, bottom layer 216 can be partially etched using either chemical etching or electrochemical machining through a mask (also sometimes referred to as "electroetching" or "electrochemical micromachining"), so that it has a rounded shape (e.g., a half circular cross-sectional shape).

In FIG. 4C, flow through internal channel 210 is defined in top layer 212, such that the thickness of material remaining between the channel 210 and the top surface 212 is sufficiently small that significant strain is created. This version presents the advantage that an area of the top layer 212 (i.e., the diaphragm) that experiences the largest amount of strain does not have a sharp corner, which causes mechanical stress concentration and could lead to crack initiation and failure over time. Preferably bottom layer 216 is thicker than a portion of the top layer 212 (i.e., the diaphragm) so that its deformation is much smaller than that of the top layer.

In FIG. 4D, flow through channel 210 is created by replication using electrochemical machining and a tool that has a rectangular shape with rounded corners creating a substantially arcuate cross-sectional shape. By plunging the tool into layer 212, a flexure membrane 220 (i.e., the diaphragm) with precisely controlled thickness is created. As in the embodiment shown in FIG. 4C, the rounded corners minimize stress concentrations at the edges of the flexure.

A further advantage of the use of electrochemical machining as provided to form the embodiments shown in FIGS. 4C and 4D is the achievement of smooth surfaces, with surface roughness as low as 25 nanometers, or lower. This minimizes the presence of surface asperities that constitute locations of stress concentration and initiation sites for cracks and fatigue failure.

The embodiments shown in FIGS. 4C and 4D could also be fabricated using milling, possibly with ball end mills that can create rounded corners. In this case, electropolishing might be performed after fabrication in order to remove surface asperities and achieve a smoother surface, thus again reducing risks of crack and fatigue failure. In addition, the embodiments shown in FIGS. 4C and 4D have a cross-sectional shape free of corners that may induce regions of stagnation or recirculating flow.

In some instances, the embodiments shown in FIGS. 4C and 4D are preferred over the embodiment shown in FIGS. 4A and 4B because the mechanical stresses in the corners are lower than in the straights corners of versions A and B, so that it is possible to achieve larger deflection and strain in the diaphragm.

FIGS. 4E and 4F show embodiments of devices with symmetrical constructions and two sensing elements 205A and 205B located on both the top and bottom surfaces. In the embodiment shown in FIG. 4E, the planar device 200 is made of three layers (212, 214, and 216) as in the device shown in FIG. 4A, but the bottom layer 216 has the same thickness as the top layer 212 in a region adjacent to the flow channel (i.e., a sensing region of flow through channel 210) so that both layers experience the same amount of strain, which is measured by the two sensing elements 205A and 205B located on diaphragms on opposing sides of the fluid channel 210. This effectively doubles the signal generated by the pressure sensor. In the embodiment shown in FIG. 4F, the device is made of two layers 212 and 216, which are substantially identical and have rounded semi-elliptical channels, which form an elliptical flow through channel 210 when diffusion bonded together.

Figure 5:
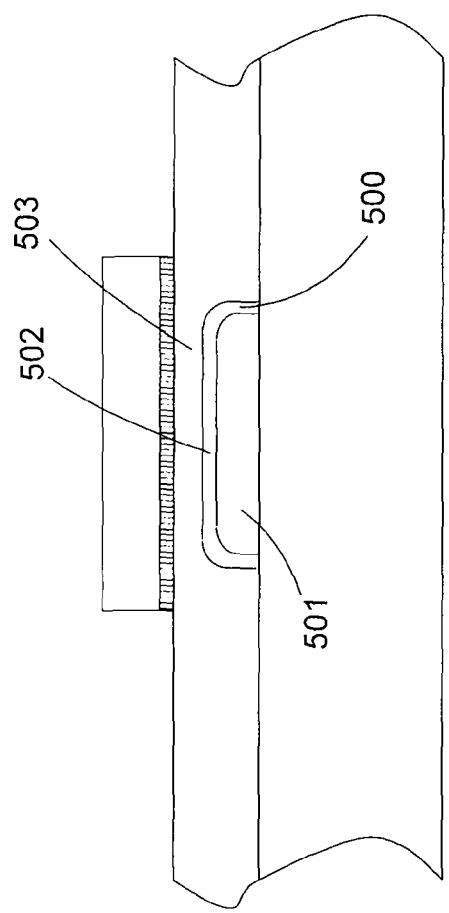
FIG. 5 is an enlarged cross-sectional view of a portion of another embodiment of a pressure sensor.

A significant deflection of the diaphragm is necessary in order to achieve good signal and accuracy of the sensing element (e.g., the strain gauge). This requires that the characteristic size of the chamber or cavity underneath the diaphragm (e.g., width for a rectangular chamber, diameter for a circular chamber) be several millimeters. If a large corner radius is selected in addition to a reduction in the stresses at the corner of the diaphragm, as in FIGS. 4D and 4E, the internal volumes of the chamber can be several tens of microliters. In some applications, when the flow rate is only a few microliters per minute, and the separation is intended to last only a few minutes, this might be too large. As shown in FIG. 5, the internal volume can be reduced by the addition of a "filler" part or member, 501, inside chamber 500, leaving only a small gap 502 between the filler member and top layer 503, and hence a small internal volume. This makes it possible to achieve an internal volume of 5 microliter or less (e.g., 4 microliters, 3 microliters, 2 microliters, 1 microliter, 0.5 microliters, 0.1 microliters). For example, if the internal volume is 5 microliter and the flow rate is 5 microliter/minute, the delay volume introduced by the sensor is only 1 minute.

EXAMPLE 2

Figure 6:
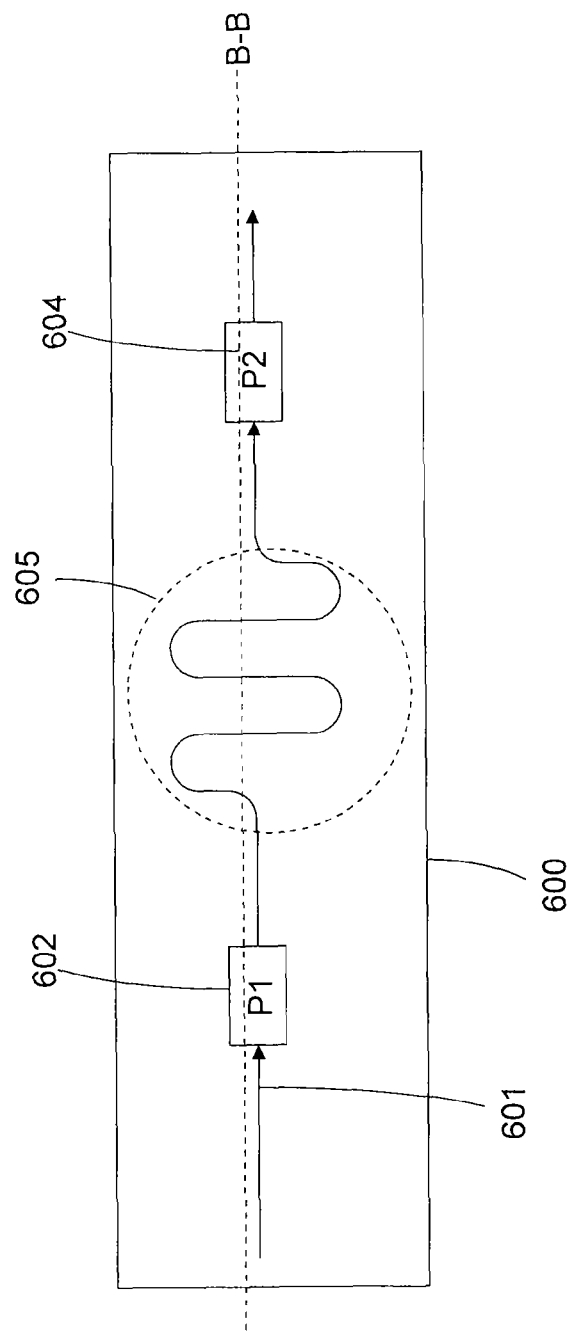
FIG. 6 is a schematic top view of a flow rate monitoring device which can withstand a high pressure environment and includes two pressure sensors separated by a flow restrictor.

This embodiment, illustrated in FIG. 6, implements a flow rate measurement, in a flow through device 600 including channel 601 by measuring the difference between the pressures read by two sensing elements P1 602 and P2 604 located at the two opposite ends of a flow restrictor 605. Fluid flows from P1 to P2 through the flow restriction 605. The flow restrictor 605 is designed to create a pressure difference ($\Delta P = P1 - P2$) that is large enough that it can be measured accurately, while at the same time not large enough that it overwhelms the backpressures generated in other parts of the chromatograph, in particular the column. To achieve this, optionally, a section of the channel between P1 and P2 has either a smaller cross-section or hydraulic diameter than the rest of the channel, or a long section of channel, such as the folded channel shown in FIG. 6, or both.

For example, for applications in nanoscale chromatography, where the flow rate ranges from 1 nanoliter/min to 100 microliters/min, a 10 centimeter long channel with diameter of 25 microns generates a pressure difference of about 0.7 MPa for a flow rate of 5 microliters/min of water at 30° C. It is preferable to realize a 10 centimeter long channel in a planar device with a limited footprint by using a folded channel, as illustrated by the restrictor 605.

Measurement of the pressures P1 and P2 and knowledge of the viscosity of the fluid flowing through the flow restrictor 605 provides a measurement of the flow rate, $Q = \Delta P / R$, where R is the fluidic resistance of the flow restrictor, which is proportional to the viscosity.

The device 600 is preferably maintained at constant temperature so that fluctuations of the fluid viscosity with temperatures and thermal drift of the sensing elements (e.g., in one embodiment, strain gauges) do not perturb the fluidic resistance measurement. If the incoming fluid is at a different temperature, it is optionally necessary to preheat this fluid to prevent temperature variations of the fluid between P1 602 and P2 604. This can be achieved on the planar device 600 itself by making the channel upstream of P1 602 sufficiently long that the fluid has time to reach thermal equilibrium with the device. If these precautions are taken, this pressure-difference sensor is optionally calibrated at a single point.

The planar device 600 made in accordance with the methods of the present technology also aids in achieving thermal regulation between P1 602 and P2 604. For example, as shown in FIG. 7A, a cross-sectional view taken along line B-B, P1 602 and P2 604 are both located on the same top layer 610. As a result, of the thermal conductance properties of the metallic material forming the top layer 610 and bottom layer 615, sensing elements P1 602 and P2 604 can be maintained at substantially the same temperature without providing active control. This aids in minimizing any differential drift that would arise if the two sensing elements were located on different substrates that would have different temperatures. Optimization of temperature maintenance can be achieved by selection of materials with high thermal conductivity and minimization of the distance between sensing elements.

Active temperature maintenance between sensing elements P1 602 and P2 604 can also be incorporated into planar devices in accordance with the technology. For example, as shown in FIG. 7B, sensing element P1 602 is located on the top layer 610 whereas sensing element P2 604 is located on the bottom layer 615. While the top layer 610 and bottom layer 615 are in thermal communication with each other due to diffusion bonding of layers (610, 615, 620) to form the device, further temperature control of the gauges P1 602 and P2 604 is provided by heater 625, which is attached to either the top or bottom surface of the planar device along with a temperature sensor 626. It should be noted that the heater 625 and the temperature sensor 626 can both be placed on the same side (i.e., both on the top surface 610 or both on the bottom surface 620).

Temperature control of devices integrating pressure sensing or flow sensing enhances performance of the fluid chromatographic instruments. This can be achieved in the devices and systems of the present technology by integration of temperature sensors and heaters on the planar device itself, or enclosure of the device in a temperature-controlled chamber. Electronic circuits for signal amplification and processing of the signals produced by the strain gauges and the temperature sensors can be integrated on the planar device, or separated from it. The electronic connections to the planar device can be integrated with the fluidic connections mentioned above.

EXAMPLE 3

Figure 8:
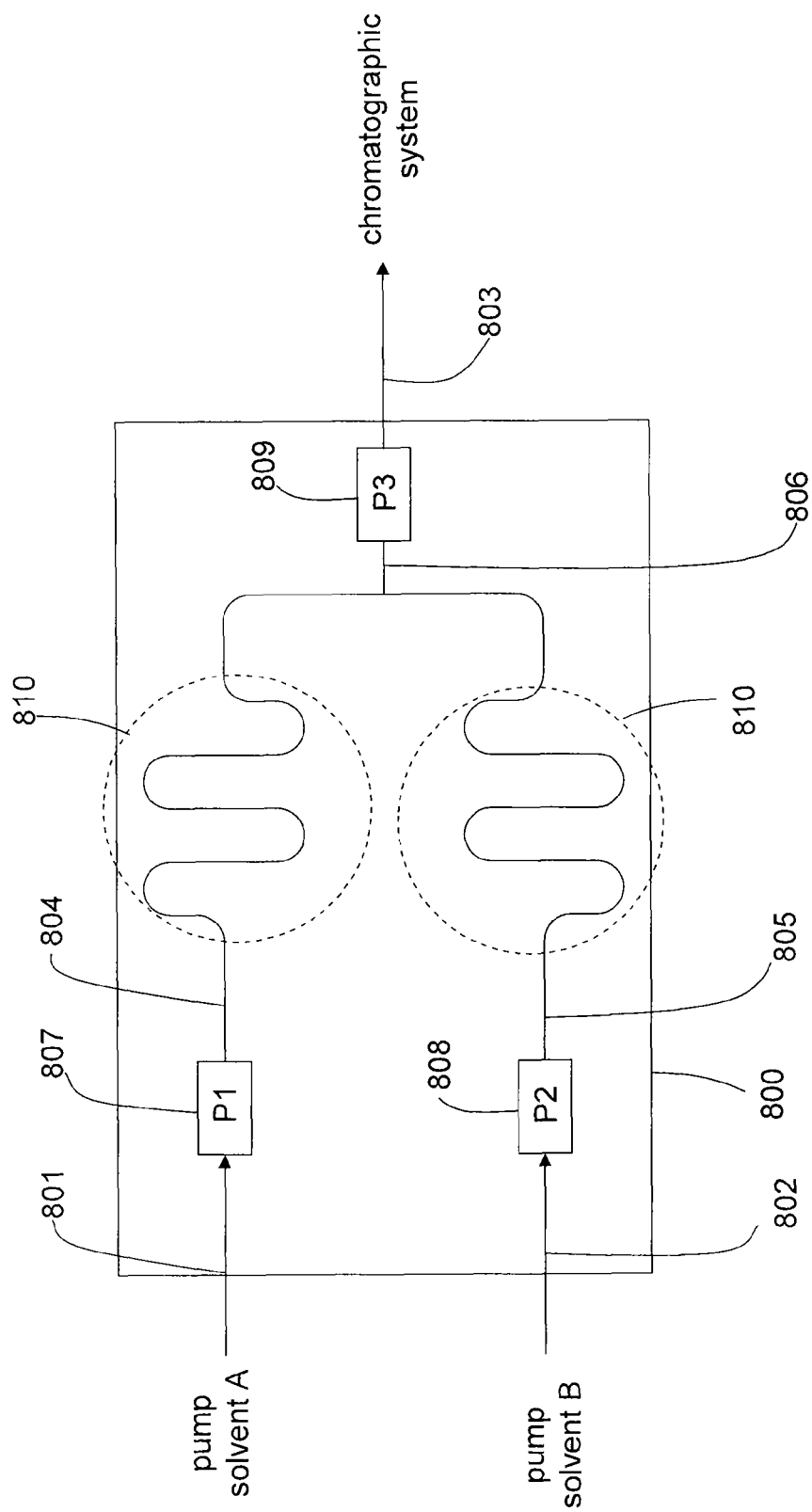
FIG. 8 is a schematic top view of a flow controller including three pressure sensors. The flow controller can be used to control fluid flow from solvent delivery pumps in a chromatography system.

FIG. 8 illustrates an embodiment that provides flow-rate measurement and control methods in a diffusion-bonded planar device, and that is useful for the generation of a mixture of two solvents with defined composition. These embodiments are optionally used to implement methods described in U.S. Pat. No. 7,674,375 ("Closed loop flow control of a HPLC constant flow pump to enable low-flow operation" incorporated by reference herein in its entirety).

Device 800 uses two pressure difference measurements, similar to the ones described above, but with one pressure sensor that is common to the two fluid flow streams. The differences of the pressures measured between P1 and P3 on one side and P2 and P3 on the other side across fluidic resistances determine the flow rates of solvents A and B, respectively.

Specifically, device 800 includes an inlet 801 for a solvent A from a first pump and an inlet 802 for a solvent B from a second pump. Device 800 also includes a single outlet 803 to a chromatographic system. Device 800 is a planar device formed from diffusion bonding several metallic parts together. Within device 800 is a fluid pathway including several portions in fluidic communication to complete a fluid circuit from the two pumps for solvent A and solvent B to the chromatographic or other fluid processing system. In particular, the fluid pathway includes a first portion 804 for fluid stream A, a second portion 805 for fluid stream B, and a fluid stream merging portion 806. Disposed on diaphragms formed within the planar device as described above are sensing elements forming pressure sensors P1 807, P2 808, and P3 809. That is, one pressure sensor formed from a sensing element (e.g., a strain gauge in one embodiment) and a diaphragm is located along each of the first portion 804, second portion 805 and the fluid merging portion 806. Also disposed along the fluid pathway are two restrictors 810 for creating fluidic resistances between the fluid merging portion 806 and each of the first and second portions 804, 805, respectively.

Device 800 also includes a controller for controlling flow from the pumps delivering solvents A and B to the device 800.

The controller (not shown) calculates a first pressure difference between P3 809 and P1 807 and a second pressure difference between P3 809 and P2 808 to calculate a flow rate of each of solvents A and B. The controller then uses this flow rate information to control the pumps for each solvent stream to control fluid flow through inlets 801 and 802.

Figure 9:
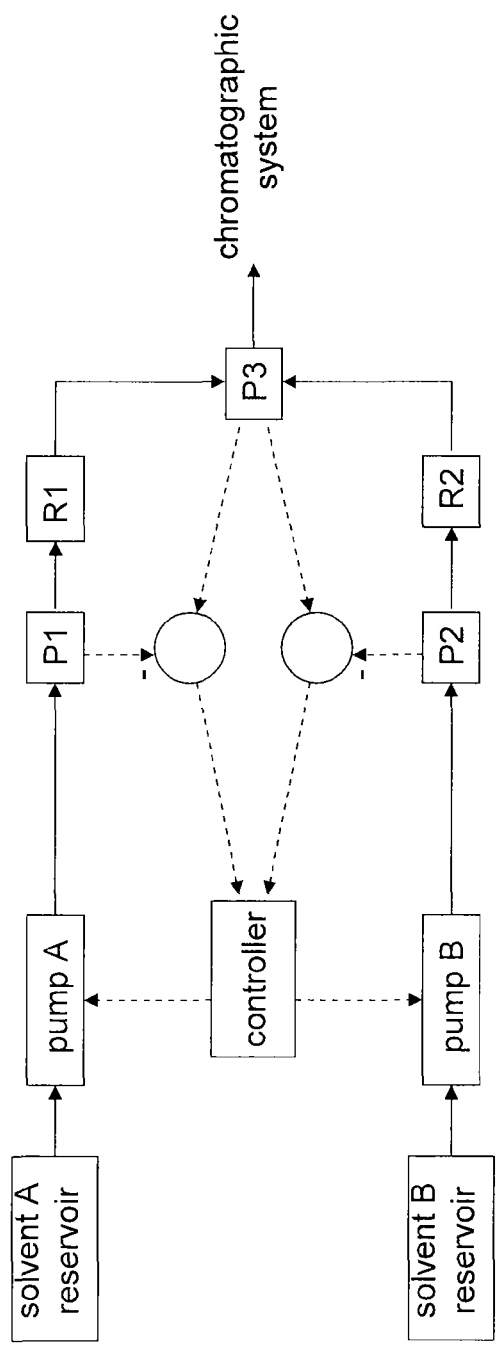
FIG. 9 is a flow chart of the control system used to control fluid flow from the solvent delivery pumps.

FIG. 9 is a flow chart of an embodiment of a method employed in flow control. Solvent A is pumped from a reservoir through pressure sensor P1, flow restrictor R1 and pressure sensor P3. The difference of the pressures measured by P3 and P1 is used by the controller to calculate the flow rate of solvent A delivered by the pump A and to control pump A. Likewise, solvent B is pumped from a reservoir through pressure sensor P2, flow restrictor R2, and pressure sensor P3, and the difference between P3 and P2 is used by the controller to calculate the flow rate of solvent B and control pump B.

One of ordinary skill in the art will recognize that a method of flow control similar to that as shown in FIG. 9 can be implemented for device 600 including two pressure sensing elements separated by a restrictor.

Figure 10:
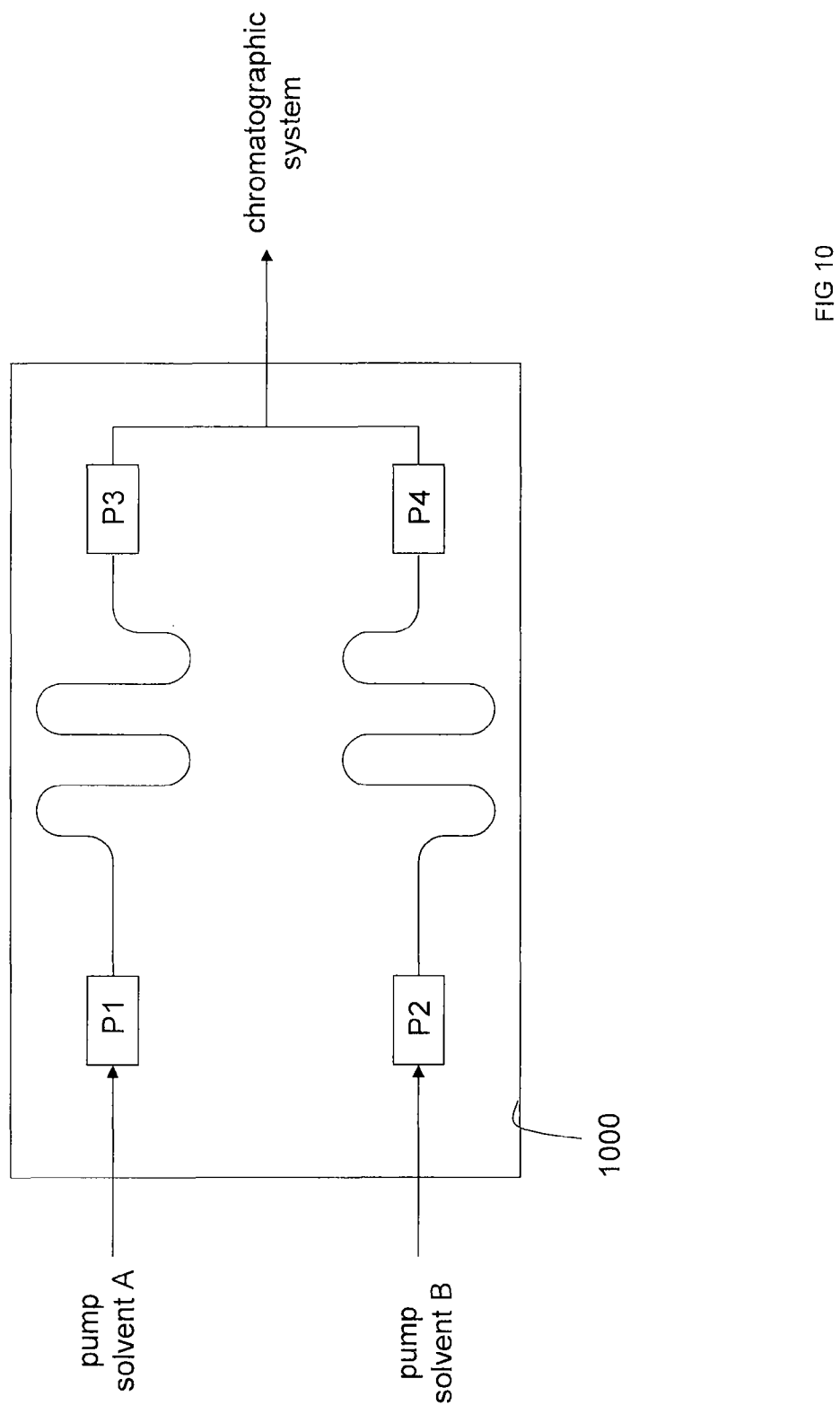
FIG. 10 is a schematic top view of a flow controller including four pressure sensors. The flow controller can be used to control fluid flow from solvent delivery pumps in a chromatography system.

It is also understood that a flow controller (i.e., device 1000) can also be constructed out of four pressure sensors, as shown in FIG. 10, by employing two separate sensors (P3 and P4 in FIG. 10) downstream of the flow restrictors instead of one common sensor (P3 in FIG. 8).

As described in previous embodiments, devices 800 and 1000 are preferably at a well-defined and controlled temperature for the flow rate measurements to be accurate and preheating is optionally used to equalize the temperature of the incoming solvents and that of the device.

Planar devices made by diffusion-bonding optionally integrate other functionalities beside pressure and flow sensing, such as solvent mixing, solvent preheating, sample injection, and a direct interface to a column.

Titanium and titanium alloys such as Ti-6Al-4V are preferred metallic materials for the layers used to make the planar devices, but, other materials, such as 300 series stainless steel are optionally suitable, as noted above.

If the fluid flowing in a channel inside a planar device contains molecules of interest in the chemical separation performed by the chromatography instrument, the wetted surface is optionally coated or passivated (i.e., the wetted surface is modified) after diffusion bonding of the planar device in order to prevent or reduce adsorption of analytes onto the internal surfaces of the device or leaching of metallic ions into the fluid streams. A well-known example of such adsorption is the binding of phosphopeptides onto titanium dioxide. The coating or passivation process is sometimes referred to as surface modification.

To form the planar devices in accordance to the present technology, two or more metallic parts are diffusion bonded together such that the planar device has a top surface, a bottom surface, and at least one channel disposed between the top and bottom surfaces. A sensing element is attached to a diaphragm formed in at least one of the top or bottom surface. The diaphragm is located above a sensing region of the flow channel (preferably having an internal wetted volume of about 25 microliters or less, and more preferably having an internal wetted volume of about 5 microliters or less) and is sized to deflect in response to fluid pressure therein. In some embodiments, the diaphragm can deflect up to about 20 microns. In some instances, this amount of deflection allows for greater resolution in measurement by the sensing element. While deflection of the diaphragm does increase the amount of internal wetted volume of the planar device, the increase is very small (e.g., insubstantial), typically smaller than 1% of the internal volume of the cavity, and has no negative effect on the flow characteristics.

To form the channel in the metallic parts, the parts are patterned, such as by chemical etching, electron beam cutting, electrochemical machining, or mechanical milling. In some embodiments, the metallic parts are patterned such that at least the sensing region has a substantially arcuate cross-sectional shape (e.g., partially circular, circular, partially elliptical, elliptical, oblong with rounded corners).

This method can be used to integrate multiple sensing elements onto a single substrate in order to build multiple pressure sensors on a single flow through planar device. For example, the top layer of the planar device can be modified to include multiple diaphragms for attachment of multiple strain gauges. Similarly, the bottom surface can be modified to include multiple diaphragms for attachment of multiple strain gauges. Further, each of the top and bottom surfaces can be modified for the attachment of one or more sensing elements, including the modification of top and bottom surfaces to include diaphragms surrounding the substantially the same sensing region of the flow channel.

Although several embodiments of the technology have been described, it will be apparent to a person of ordinary skill in the art that various modifications to the details thereof shown and described may be made without departing from the scope of the claims.

What is claimed is:

1. A flow through pressure sensor for use in a system for chromatographic separation, the flow through pressure sensor able to withstand pressures of at least about 40 megapascals and comprising:
   a planar device formed from a plurality of metallic parts attached by diffusion bonding, the planar device having a top surface, a bottom surface, and at least one flow through channel disposed between the top and bottom surfaces; and
   a sensing element located on a diaphragm formed from a portion of at least one of the top surface or bottom surface of the planar device, the diaphragm bounding one face of a first sensing region of the at least one flow through channel and being sized to deflect a distance in response to fluid pressure in the first sensing region, the first sensing region having an internal volume of about 25 microliters or less.

2. The flow through pressure sensor according to claim 1, wherein the sensing element measures mechanical strain of the diaphragm for use in calculating fluid pressure in the first sensing region of the at least one flow through channel.

3. The flow through pressure sensor according to claim 1, wherein the sensing element measures deflection of the diaphragm for use in calculating fluid pressure in the first sensing region of the at least one flow through channel.

4. The flow through pressure sensor according to claim 1, wherein the internal volume is between about 25 microliters and 5 microliters.

5. The flow through pressure sensor according to claim 1, wherein the internal volume is between about 5 microliters and 0.5 microliters.

6. The flow through pressure sensor according to claim 1, wherein the portion forming the diaphragm is from the top surface of the planar device.

7. The flow through pressure sensor according to claim 6, further comprising a second sensing element located on a second diaphragm, the second diaphragm formed from a portion of the bottom surface of the planar device and opposing the diaphragm formed from the top surface.

8. The flow through pressure sensor according to claim 1, further comprising a second sensing element, the second sensing element located on a second diaphragm formed from a second portion of at least one of the top surface or bottom surface of the planar device, the second diaphragm bounding one face of a second sensing region and being sized to deflect a distance in response to fluid pressure in the second sensing region, the second sensing region having an internal volume of about 25 microliters or less.

9. The flow through pressure sensor according to claim 8, further comprising a flow restrictor positioned between the first and second sensing regions of the at least one flow through channel.

10. The flow through pressure sensor according to claim 8, wherein the first and second sensing elements are both located on either the top surface or the bottom surface.

11. The flow through pressure sensor according to claim 8, wherein the first diaphragm is formed from the top surface and the second diaphragm is formed from the bottom surface.

12. The flow through pressure sensor according to claim 8, wherein the first and second sensing elements are at substantially the same temperature.

13. The flow through pressure sensor according to claim 1, further comprising a plurality of sensing elements, each sensing element of the plurality located on a separate diaphragm formed from a separate portion of at least one of the top surface or bottom surface of the planar device, each of the separate diaphragms bounding one face of each separate sensing region of the at least one flow through channel, each of the separate sensing regions having an internal volume of 25 microliters or less, and each of the separate diaphragms being sized to deflect a distance in response to fluid pressure in a corresponding separate sensing region of the at least one flow through channel.

14. The flow through pressure sensor according to claim 13, wherein the plurality of sensing elements are at substantially the same temperature.

15. The flow through pressure sensor according to claim 1, wherein the plurality of metallic parts comprises a material that is compatible with a fluid mobile phase used in the chromatographic separation.

16. The flow through pressure sensor according to claim 1, wherein individual metallic parts of the plurality of metallic parts comprises titanium or a titanium alloy.

17. The flow through pressure sensor according to claim 1, wherein the plurality of metallic parts comprises stainless steel.

18. The flow through pressure sensor according to claim 1, wherein the first sensing region is defined by an arcuate cross-sectional shape.

19. The flow through pressure sensor according to claim 18, wherein the arcuate cross-sectional shape is circular.

20. The flow through pressure sensor according to claim 18, wherein the arcuate cross-sectional shape is elliptical.

21. The flow through pressure sensor according to claim 1, wherein the first sensing region is defined by a cross-sectional shape free of corners that induce regions of stagnation or recirculating flow.

22. The flow through pressure sensor of claim 1, wherein the first sensing region includes a filler member to reduce the internal volume to less than about 25 microliters.

23. The flow through pressure sensor of claim 1, wherein the flow through pressure sensor is used in a system including liquid chromatographic separations, the flow through pressure sensor being adapted for operation at a flow rate of less than about 50 microliters/minute.

24. The flow through pressure sensor of claim 1, wherein the flow through pressure sensor is used in a system including supercritical fluid chromatographic separations, the flow through pressure sensor being adapted for operation at a flow rate of less than about 400 microliters/minute.

\* \* \* \* \*